United States Patent [19]

Rosa

[11] Patent Number: 5,279,938
[45] Date of Patent: Jan. 18, 1994

[54] SENSITIVE DIAGNOSTIC TEST FOR LYME DISEASE

[75] Inventor: Patricia A. Rosa, Hamilton, Mont.

[73] Assignee: The United States of America as represented by the Department of Health and Human Services, Washington, D.C.

[21] Appl. No.: 885,077

[22] Filed: May 18, 1992

Related U.S. Application Data

[63] Continuation of Ser. No. 361,850, Jun. 5, 1989, abandoned.

[51] Int. Cl.$^5$ .................. C12Q 1/68; C12P 19/34; C07H 5/04; C07H 17/00
[52] U.S. Cl. .................. 435/6; 435/320.1; 536/12.7; 536/23.1; 536/24.3; 536/24.33; 536/25.4
[58] Field of Search .................. 536/27, 18.7, 23.1, 536/24.3, 24.33, 25.4; 435/6, 91

[56] References Cited

U.S. PATENT DOCUMENTS 4,683,202  7/1987  Mullis .................. 435/91

OTHER PUBLICATIONS

Schwan et al., "Ethiacy of Nucleic Acid Hybridization Probes ..." Annals of the N.Y. Academy of Science, vol. 539, pp. 419–420.
Goodman et al., "A Unique DNA Clone Specific for Borrelia ..." Clin. Res. vol. 37(2) 1989.
Rosa, et al., "A Specific and Sensitive Assay for the Lyme Disease Spirochete Borretia burgdorferi Using the Polymerase Chain Reaction", The Jour. of Infect. Dis., vol. 160, No. 6, Dec., 1989, pp. 1018–1029.
Schwan, et al., "Efficacy of Nucleic Acid Hybridizaation Probes for the Detection and Identification of Borrelia burgdorferi" Annals of the N.Y. Academy of Sciences, vol. 539, pp. 419–421 (1988).
Goodman, et al., "A Unique DNA Clone Specific for Borrelia burgdoferi: Preliminary Hybridization and Sequence Analysis" Clin. Res., vol. 37 (2), pp. 429A (1989).
Rosa, et al., "A Specific and Sensitive Assay for the Lyme Disease Spirochete Borrelia burgdorferi Using the Polymerase Chain Reaction", J. of Infect. Dis., vol. 160 (6), pp. 1018–1029 (Dec. 1989).

Primary Examiner—Robert A. Wax
Assistant Examiner—Miguel Escully
Attorney, Agent, or Firm—Morgan & Finnegan

[57] ABSTRACT

The nucleotide sequence of a recombinant clone containing a specific segment of Borrelia burgdorferi DNA which enables the identification of the spirochetes causing Lyme disease has been provided. A diagnostic kit containing oligonucleotide primers derived from this sequence, suitable for the detection of Borrelia burgdoferi in a PCR assay, as well as the cloned DNA of the present invention, allows the detection of Lyme disease with sensitivity and specificity not heretofore attained by any other test.

6 Claims, 8 Drawing Sheets

FIG. 2

```
                         →
                         A
5'  GATCAAAA CG AAGATACTAA ATCTGT AATT GCAGAAACAC CTTTTGAATT
3'  CTAGTTTGC TTCTATGATT TAGACATTAA CGTCTTTGTG GAAAACTTAA

51  AAATTTTGGC TTGTCAGGAG CCTATGGAAA CGAGACATTC AATAATTCAT
    TTTAAAACCG AACAGTCCTC GGATACCTTT GCTCTGTAAG TTATTAAGTA

101 CAATAACATA CTCTTTAAAA GATAAATCCG TAGTTGGCAA CGATTTATTG
    GTTATTGTAT GAGAAATTTT CTATTTAGGC ATCAACCGTT GCTAAATAAC

151 AGCCCAACTT TATCAAATTC TGCAATTTTA GCATCTTTTG GAGCTAAATA
    TCGGGTTGAA ATAGTTTAAG ACGTTAAAAT CGTAGAAAAC CTCGATTTAT

201 TAAGCTTGGA TTAACAAAAA TAAACGATAA AAATACCTAT CTTATTTTGC
    ATTCGAACCT AATTGTTTTT ATTTGCTATT TTTATGGATA GAATAAA ACG

251 AAATGGGAAC TGATTTTGGA ATAGATCCTT TTGCAAGGGA TTTTTCTATA
    TTTACCCTTG ACTAA AACCT TATCTAGGAA AACGTTCCCT AAAAAGATAT
              ←
              B
301 TTGGACACA TCTCAAAAGC AGCGAATTTC AAAAAGAAA CACCCTCAGA
    AAACCTGTGT AGAGTTTCG TCGCTTAAAG TTTTTTCTTT GTGGGAGTCT

351 TCCTAACAAA AAAGCTGAAA TATTTGATC 3'
    AGGATTGTTT T TTCGACTTT ATAAACTAG  5'
                 ←
                 C
```

SENSITIVE DIAGNOSTIC TEST FOR LYME DISEASE

This is a continuation of co-pending application Ser. No. 07/361,850, filed on Jun. 5, 1989, now abandoned.

The present invention relates generally to diagnostic tests, particularly to assays and kits. More particularly, the present invention relates to a diagnostic kit comprising containers containing various components for performing a sensitive and specific assay for detecting the presence of Lyme disease spirochetes.

Lyme disease has been demonstrated to be caused by a pathogenic spirochete *Borrelia burgdorferi* which infects a broad range of vertebrates (Burgdorfer, W., 1986, *Rev. Infect. Dis.*, 6: 932-940). Lyme disease is a severe human illness with worldwide endemic foci. Transmission of Lyme disease occurs primarily via infected ticks of the Ixodes complex (Burgdorfer, W., 1984, *Yale J. Biol. Med.*, 57: 71-76)

Diagnosis of Lyme disease is often not straightforward. There exist well-documented cases of Lyme disease where knowledge of tick bite, skin rash or positive serology are missing (Magnarelli, et al, 1987, *J. Infect. Dis*, 156: 183-187; Craft et al, 1984, *J. Infect. Dis.*, 149: 789-795; Dattwyler et al, 1988, *N. Engl. J. Med.*, 319: 1441-1446). Most of the systemic manifestations of advanced Lyme disease are not unique and demonstration of spirochetes in patients is extremely difficult (Steere, et al, 1983, *N. Engl. J. Med.*, 308: 733-740). Considering the debilitating nature of the advanced stages of the disease, an accurate diagnostic tool remains a critical need.

SUMMARY OF THE INVENTION

It is, therefore, an object of the present invention to provide a reliable, sensitive and specific tool which distinctively detects the presence of even a single spirochete of *B. burgdorferi* in humans, domestic animals, wild animals, insects or in any other infected source.

It is another object of the present invention to provide means for confirming or denying the identity of a spirochete as *Borrelia burgdorferi*.

It is a further object of the present invention to provide a clone of a specific segment of *B. burgdorferi* chromosonal DNA and the complete nucleotide sequence of said segment.

It is an additional object of the present invention to provide a diagnostic test for Lyme disease.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 shows the nucleotide sequence of *B. burgdorferi* clone 2H1. Single-stranded oligos corresponding to sequences designated A and C represent the PCR primers. Oligo B represents an internal probe used to confirm the identity of the PCR amplified fragments.

Figure 1A:
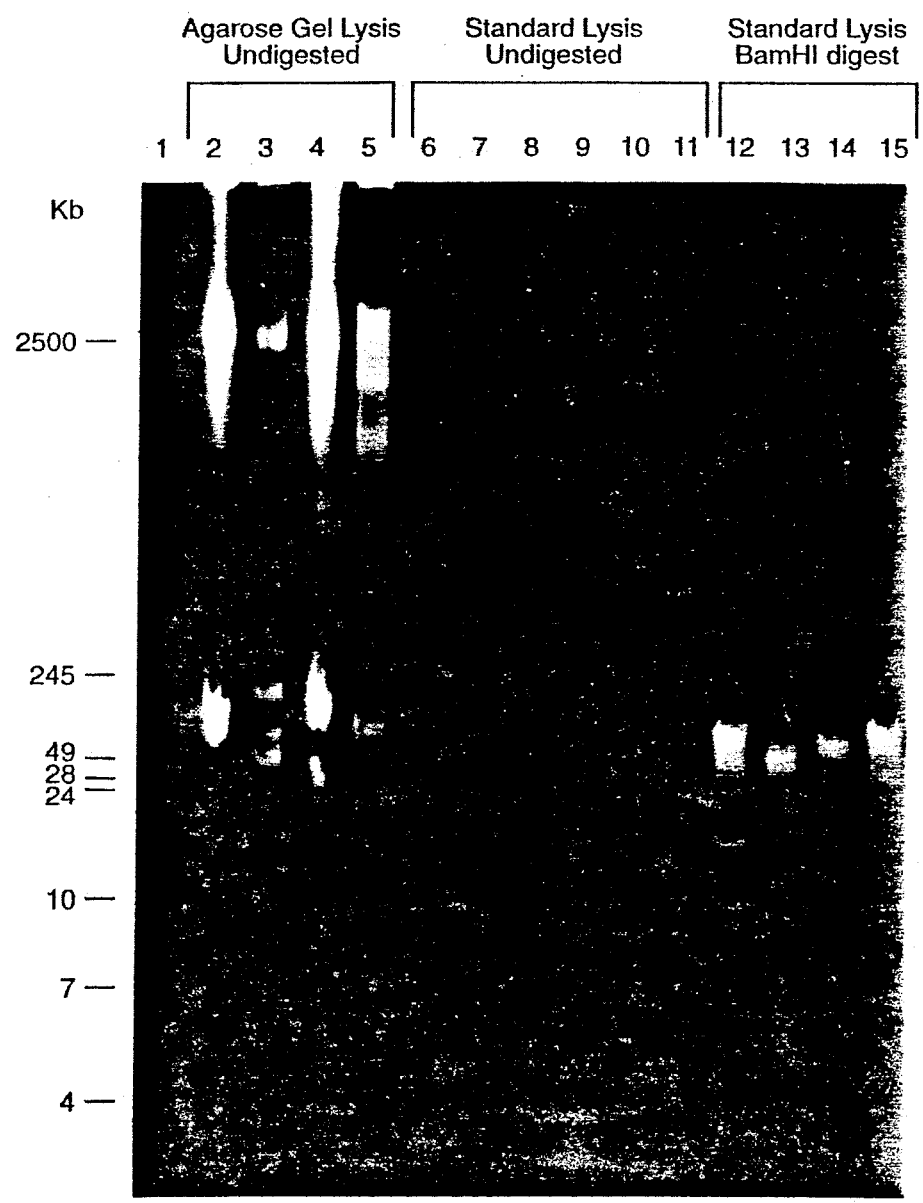
FIGS. 1(A-C) show the results of genomic Southern analyses of Borrelia DNA probed with randomly cloned *B. burgdorferi* sequences. (A) Ethidium bromide-stained field inversion gel run for 17 hr at 150 volts. Electrophoresis conditions were as follows: initial reverse time—0.1 second; reverse increment—0.1 second; initial forward time—0.3 second; forward increment—0.3 second; number of steps—100. (B) Blot prepared from the gel shown in part A, hybridized with clone 3A18. (C) Blot prepared from a field inversion gel run for 20 hr at 100 volts, hybridized with clone 2H7. Electrophoresis parameters were as follows: initial reverse time—0.05 second; reverse increment—0.01 second; initial forward time—0.15 second; forward increment—0.03 second; number of steps—48; reverse increment increment—0.001 second; forward increment increment—0.003 second. The DNAs are as follows: Lane 1—undigested and HindIII lambda standards; Lane 2—*B. burgdorferi* HB19; Lane 3—*B. hermsii* HS1; Lane 4—*B. burgdorferi* B31; Lane 5—*Saccharomyces cerevisae*; Lane 6—*B. burgdorferi* B31; Lane 7—*B. hermsii* HS1; Lane 8—*B. burgdorferi* HB19; Lane 9—*B. burgdorferi* G1; Lane 10—*B. burgdorferi* Sh.2.82; Lane 11—*B. burgdorferi* G2; Lane 12—*B. burgdorferi* B31; Lane 13—*B. hermsii* HS1; Lane 14—*B. burgdorferi* HB19; Lane 15—*B. burgdorferi* G1. The sizes and mobilities of the DNA standards are indicated at the left of each figure. The arrow at the left of FIG. 1C indicates the mobility of the largest yeast chromosomes on this gel. Yeast chromosome markers were run adjacent to lambda concatemers on a similar gel to determine their sizes. Chromosomes XII (2500 kb) and IV (1600 kb) were not resolved.

FIGS. 5(A-B) demonstrate the sensitivity of *B. burgdorferi* PCR assay. 10-fold serial dilutions of purified *B. burgdorferi* B31 DNA (5A, Lanes 2-7) and crude culture lysates (5B, Lanes 10-21) were amplified and 1/20 of the reaction analyzed on a gel. The quantity of template DNA in the reaction and the number of cycles amplified were as follows: Lane 2-100 ng, 15 cycles; Lane 3-10 ng, 20 cycles; Lane 4—1 ng, 25 cycles; Lane 5—100 pg, 25 cycles; Lane 6—10 pg, 30 cycles; Lane 7—1 pg, 30 cycles; Lane 8—0 DNA, 30 cycles; Lane 9—0 DNA, 45 cycles; Lane 10—*B. hermsii*, 100 µl, 45 cycles; Lane 11—*B. burgdorferi* SH.2.82, 100 µl, 15 cycles; Lane 12—*B. burgdorferi* HB19, 100 µl, 15 cycles; Lane 14—*B. burgdorferi* B31, 100 µl, 15 cycles; Lane 15 *B. burgdorferi* B31, 10 µl, 20 cycles; Lane 16—*B. burgdorferi* B31, 1 µl, 25 cycles; Lane 17—*B. burgdorferi* B31, $10^{-1}$ µl, 25 cycles; Lane 18—*B. burgdorferi* B31, $10^{-2}$ µl 30 cycles; Lane 19—*B. burgdorferi* B31, $10^{-3}$ µl, 35 cycles; Lane 20—*B. burgdorferi* B31, $10^{-4}$ µl, 40 cycles; Lane 21—*B. burgdorferi* B31, $10^{-5}$ µl, 45 cycles. Hin F pBR322 standards were run in Lanes 1 and 13; the sizes and mobilities are indicated to the left of each figure.

FIGS. 6(A-B) show the distinguishing feature and specificity of *B. burgdorferi* PCR assay performed in the excess of eukaryotic DNA. 100 ng of *B. burgdorferi* B31 DNA was amplified for 15 cycles in the presence of 1 microgram (lane 1), 100 ng (lane 4), or no (lane 3), eukaryotic DNA and 1/20 of the reaction analyzed on a gel. The ethidium bromide-stained gel is shown in (A) and a blot prepared from this gel and hybridized to an internal probe (oligo B) is shown in (B). Lanes 5-15: 10-fold serial dilutions of *B. burgdorferi* B31 DNA were amplified in the presence of 100 ng of eukaryotic DNA and 1/20 of the reaction analyzed on a gel. The quantity of *B. burgdorferi* B31 DNA in the reaction and the number of cycles amplified were as follows: lane 5—10 ng. 20 cycles; lane 6—1 ng, 20 cycles; lane 7—1 ng, 25 cycles; lane 8—$10^{-1}$ ng, 25 cycles; lane 9—$10^{-1}$ ng, 30 cycles; lane 10—$10^{-2}$ ng, 30 cycles; lane 11—$10^{-2}$ ng, 35 cycles; lane 12—$10^{-3}$ ng, 35 cycles; lane 13—$10^{-3}$ ng, 40 cycles; lane 14—$10^{-4}$ ng, 40 cycles; lane 15—0 ng, 40 cycles, Hin F pBR322 size standards were run in lane 2. The upper band of the doublet on the autoradiograph (B) represents the single-stranded, denatured form of the fragment. It is not as pronounced on the ethidium bromide-stained gel (A) because single-stranded DNA binds DNA much less efficiently than double-stranded.

DETAILED DESCRIPTION OF THE INVENTION

The above and various other objects and advantages of the present invention are achieved by amplifying DNA obtained from the skin, body fluid or cellular specimen of a person, animal, insect, and the like suspected of being infected with *Borrelia burgdoferi*, by polymerase chain reaction (PCR), an amplified fragment of the appropriate size being indicative of the presence of *B. burgdorferi*. When necessary, the identity of the amplified fragment can be confirmed by hybridizing with the cloned DNA of *B. burgdoferi*. The demonstration of *Borrelia burgdoferi* in humans provides the basis for a diagnosis of Lyme Disease.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

Borrelia Strains and Cultivation

The spirochetes used in this study came from the following sources. *B. burgdorferi* B31 (ATCC 35210), the prototype strain, originated from *Ixodes dammini* from Shelter Island, N.Y. (Burgdorfer et al, 1982, *Science*, 216: 1317-1319; Johnson et al, 1984, *Int. J. Syst. Bacteriol.*, 34: 496-497; Steere et al, supra). *B. burgdorferi* ECMM-NY-86 was isolated from an erythema chronicum migrans lesion of a patient in New York in 1986 (Schwan et al, 1988, *J. Clin. Microbiol.*, 26: 893-895). *B. burgdorferi* SH-2-82 was isolated from naturally infected *I. dammini* collected on Shelter Island, N.Y., in 1982 (Schwan et al, supra). *B. burgdorferi* CA-2-87 was isolated from a pool of eight adult *Ixodes pacificus* collected in Tulare County, Calif. in 1987 (Schwan et al., supra). *B. burgdorferi* JD-1 originated from naturally infected nymphal *I. dammini* collected at Crane's Beach, Ipswich, Mass. (Piesman et al., 1987, *J. Clin. Microbiol.*, 25: 557-558). *B. burgdorferi* G-1 and G-2 were isolated from human cerebral spinal fluid in Germany (Huppertz et al., 1986, lancet, 2: 1468-1469). *B. hermsii* HS1 serotype C (ATCC 35209) originated from *Onithodoros hermsii* collected near Spokane, Wash. (Stoenner et al., 1982, *J. Exp. Med.*, 156: 1297-1311). *B. hermsii* FG was isolated at Rocky Mountain Laboratories (RML) in April 1987 from the blood of an 8-year-old boy from Seattle, Wash. *B. coriaceae* Co53 (ATCC 43381) originated from *O. coriaceus* from California (Johnson et al., 1987, *Int. J. Syst. Bacteriol.*, 37: 72-74; Lane et al., 1985, *Science*, 230: 85-87). *B. parkeri*, *B. turicatae*, *B. anserina*, and *B. crocidurae* were in the RML bacterial pathogens collection.

Liver borrelial cultures were maintained in BSK II medium (Barbour, A. G., 1984, *J. Biol. Med.*, 57: 521-525), at 34° C. and passaged twice a week. Numbers of spirochetes were determined by dark-field microscopy, using a Petroff-Hausser counting chamber.

DNA Isolation

Total genomic DNA was prepared with modifications of a pervious protocol (Meier et al., 1985, *Cell* 41: 403-409). Briefly, spirochetes were pelleted from 100 ml of a stationary phase culture and resuspended in 5.6 ml TES (50 mM Tris, 50 mM EDTA, 15% surose, pH 8). 12 mg lysozyme (Boehringer Mannheim GmbH, West Germany) were added in 1 ml Tris (0.25M, pH8) and the sample incubated at 37° C. for 20 min. 1 mg Proteinase K (Boehringer Mannheim) and 0.33 ml of 10% sodium dodecyl sulfate (SDS) were added sequentially, and the sample was then incubated at 55° C. for 1 hr. The sample was subsequently extracted two times with phenol/chloroform (1:1) and then one time with chloroform alone. Nucleic acid was precipitated by adjusting the sale concentration to 0.3M sodium acetate and the addition of 2.5 volumes of ethanol. Precipitated DNA was spooled out with a glass rod, rinsed in 70% ethanol, and resuspended in 2.5 ml TE. This sample was then digested with RNAse A (100 μg/ml) at 37° C. for 1 hr, followed by the addition of Proteinase K (200 μg/ml) and SDS (to 0.5%) with continued incubation at 37° C. for 1 hr. The sample was then phenol/chloroform extracted, precipitated and resuspended in 2.5 ml TE, as described above. DNA concentration was determined by optical density.

Lysis of spirochetes in agarose was performed as described for the preparation of DNA inserts for restriction digests by a manufacturer (New England Biolabs, Inc., Beverly, Mass.). Agarose plugs containing undigested DNA were stored in 10 mM Tris, 100 mM EDTA, pH8 until used.

Electrophoresis

Genomic DNA was analyzed on 0.8% agarose/0.5×TBE gels (10×TBE=0.89M Tris, 0.89M Borate, 0.028M EDTA) at room temperature (about 22°-24° C.) with recirculating buffer. Field inversion electrophoresis conditions (Carle et al, 1986, *Science*, 232: 65-68) were established with a standard electrophoresis chamber (DNA sub-cell, Bio-Rad Laboratories, Richmond, Calif.) and a power inverter (PPI-200, M. J. Research, Cambridge, Mass.). Yeast chromosomal standards (*S. cerevisiae*, Bio-Rad) and bacteriophage lambda concatemers (Clontech, Palo Alto, Calif.) were purchased in agarose blocks.

PCR reaction products were analyzed on 1.5% agarose/0.5 X TBE gels with standard electrophoresis conditions (Maniatis et al, Molecular cloning. A laboratory manual. Cold Spring Harbor, N.Y.: Cold Spring Harbor Laboratory, 1982: 1-545).

Random Cloning of *B. burgdorferi* DNA sequences

A Sau3A partial digest of total genomic DNA from *B. burgdorferi* strain B31 was ligated into phosphatased, BamHI-digested pUC18 (Yanisch-Perron et al, 1985, *Gene*, 33: 103-119), and transformed into *E. coli* stain DH5α. Approximately 500 recombinant colonies were obtained per 50 ng of ligated pUC DNA. Plasmids from 60 recombinants were analyzed by gel electrophoresis and eight representative clones selected for further analysis.

Hybridizations

Southern blots were prepared from gels on nylon membranes (Biotrans, ICN Biochemicals, Irvine, Calif.) (Southern, E., 1975, *J. Mol. Biol.*, 98: 503-517). Prehybridization and hybridization buffer was 6×SSC (20×SSC=3M sodium chloride, 0.3M sodium citrate), 0.1% SDS, 0.5% nonfat dry milk, and 1 mM sodium pyrophosphate.

Plasmid probes were labeled ($\alpha^{32}$P-dATP, New England Nuclear Corp., Boston, Mass.) by random priming (Boehringer Mannheim) (Feinberg et al, 1983, *Anal. Biochem*, 132: 6-13). Hybridization with plasmids was at 50° C. Filters were rinsed and then washed for 20 min at room temperature in 1×SSC/0.5% SDS, followed by 20 min at room temperature in 0.1×SSC/0.5% SDS. Oligonucleotide probes were end-labeled ($\tau^{32}$P-ATP, New England Nuclear) with T4 polynucleotide kinase (Boehringer Mannheim) (Maxam et al, 1980, *Methods Enzymol*, 65: 499-560). Hybridization with oligos was at 37° C. Filters were washed with a tetramethylammonium chloride solution at 45° C. as described by Wood et al (1985, *Proc. Natl. Acad. Sci. USA*, 82: 1585-1588).

Sequencing

The complete sequence of the insert in clone 2H1 was determined using a modification of the dideoxy chain termination technique (Sanger et al, 1977, *Proc. Natl. Acad. Sci. USA*, 74: 5463-5467) for double stranded DNA (Bartlett et al, 1986, *BioTechniques*, 4: 208-210). Plasmid DNA was prepared by a quick-boil procedure (Toneguzzo et al, 1988, *BioTechniques* 6: 460-469). Overlapping sequences were initially obtained off M13 primers from flanking vector sequences at each end. Oligo primers to insert sequences were then used to extend the sequence across both strands.

Polymerase Chain Reaction

GENE-AMP reagents (Perkin Elmer Cetus, Norwalk, Conn.) were used with an automated DNA thermal cycler (Perkin Elmer Cetus). Reaction volumes were 100 μl. Samples were denatured at 94° C. for 1 min. annealed at 37° C. for 30 sec and extended at 60° C. for 1 min. The total number of cycles were as indicated in the figure legends. For crude culture lysates, 100 μl was pelleted, spirochetes were resuspended in 10 μl TE (10 mM Tris, 1 mM EDTA, pH8) and heated to 100° C. for 10 min. Ten-fold serial dilutions were subsequently made in 10 μl TE. The volume was increased to 100 μl with PCR reaction mix.

RESULTS

*B. burgdorferi* genomic clones

The nucleotide sequence flanking a target segment of DNA must be known in order to develop a PCR assay. To this end, the initial goal was to identify and sequence an appropriate target segment of *B. burgdorferi* DNA. Total genomic DNA of *B. burgdorferi* strain B31 was fragmented with a restriction enzyme and cloned into an *E. coli* plasmid vector. Recombinants were analyzed by gel electrophoresis and eight clones with inserts ranging from approximately 100 to 10,000 base pairs (bp) were chosen for further investigation. In order to assess the suitability of these randomly cloned sequences as potential targets in a *B. burgdorferi*-specific PCR assay, genomic southern hybridizations were performed (FIG. 1).

Figure 1B:
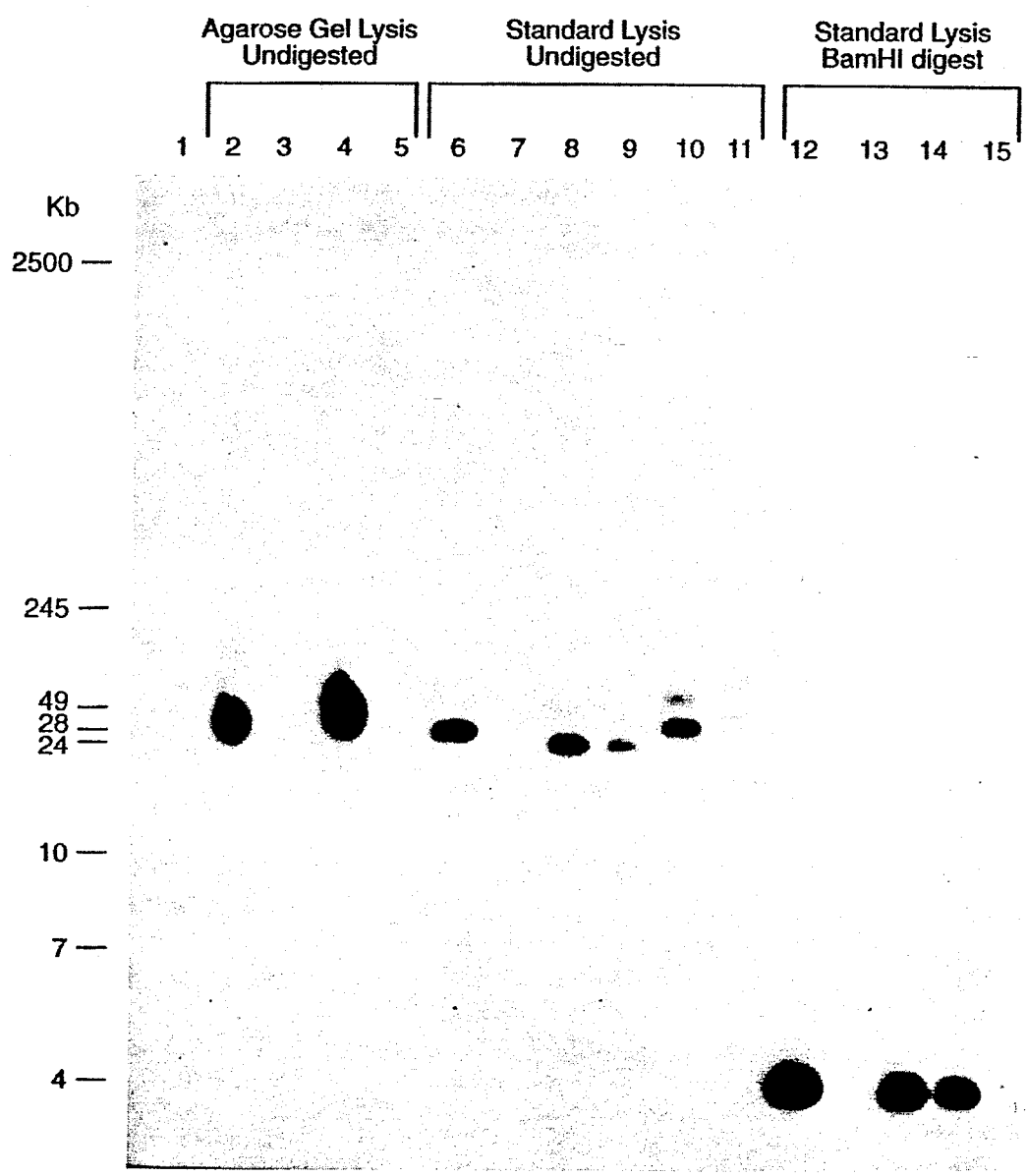
Figure 1C:
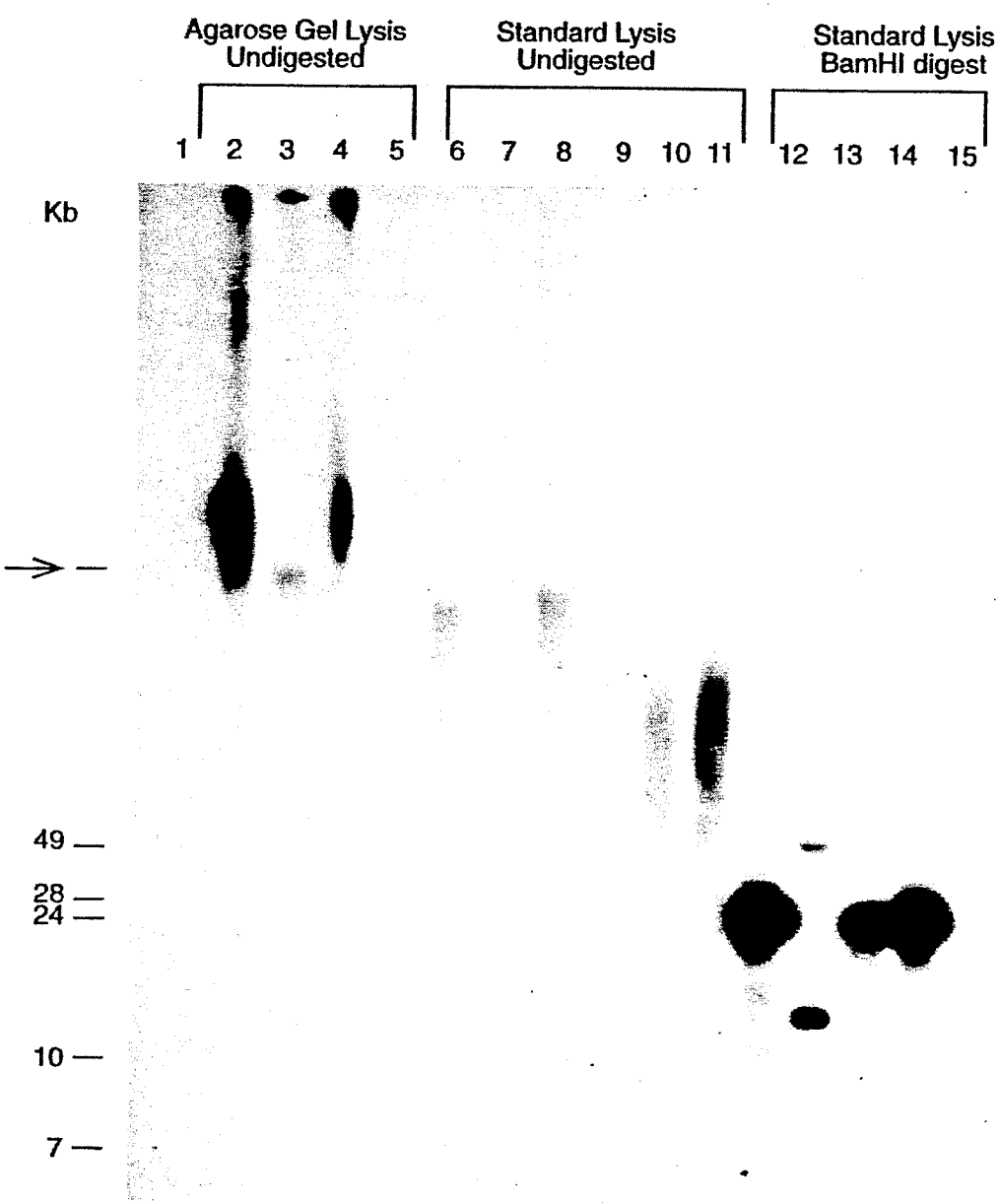

FIG. 1A shows an ethidium-bromide stained agarose gel containing total genomic DNA separated by field inversion electrophoresis from *B. hermsii* and five different *B. burgdorferi* isolates. The genomes of *B. burgdorferi* and *B. hermsii* consist of two distinct fractions (plasmid and chromosomal). Five randomly cloned *B. burgdorferi* sequences hybridized to chromosomal DNA while three clones hybridized to either the 49-kb or 19-kb plasmids of strain B31. Hybridization patterns obtained with representative clones of plasmid or chromosomal origin are shown in FIGS. 1B and 1C, respectively. All eight randomly cloned sequences of *B. burgdorferi* strain B31 hybridized to DNA from the four additional *B. burgdorferi* strains tested. Only two clones with large inserts showed slight cross-reactivity with *B. hermsii* DNA. These data are summarized in Table 1.

When alternating field electrophoresis conditions appropriate for resolving very large DNA molecules are used, a distinct chromosomal fraction is apparent only when cells have been lysed in agarose blocks (FIG.

1A, lanes 2–5). Standard lysis and extraction procedures result in randomly sheared DNA which does not migrate as a discrete species (FIG. 1A, lanes 6–11). Hybridization with clones of chromosomal origin to total undigested DNA extracted by standard procedures results in a rather faint, indiscrete signal (FIG. 2C, lanes 6–11). Hybridization to the same DNA after BamHI digestion results in a distinct band (FIG. 2C, lanes 12–15). This reflects the heterogenous, yet still fairly large, nature of the undigested, randomly sheared chromosomal DNA following standard extraction procedures.

Development of a PCR Assay

Figure 3A:
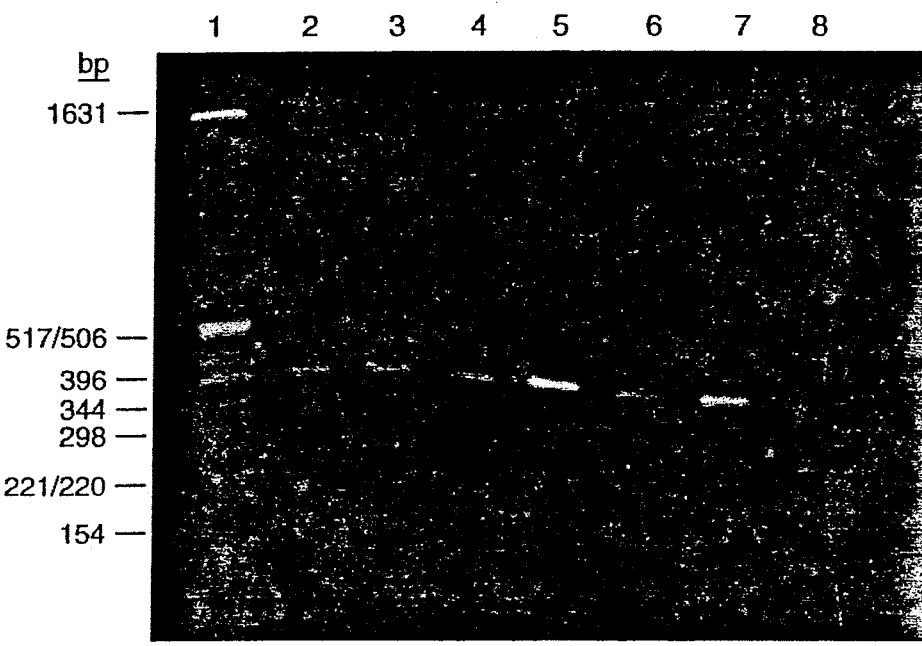
FIGS. 3(A-B) show the results of PCR amplification of *B. burgdorferi* sequences. Total genomic *B. burgdorferi* and *B. hermsii* DNA were amplified for 15 and 30 cycles, respectively. Plasmid 2H1 DNA was amplified for 15 cycles as a positive control. An ethidium bromide-stained gel on which were run 1/10 of the reactions is shown in (A). A blot prepared from this gel and hybridized to an internal probe (oligo B) is shown in (B). The source and amount of DNA in the PCR reactions are as follows: Lane 2—*B. burgdorferi* G1, 100 ng; Lane 3—*B. burgdorferi* SH.2.82, 100 ng; Lane 4—*B. burgdorferi* HB19, 100 ng; Lane 5—*B. burgdorferi* B31, 100 ng; Lane 6—*B. burgdorferi* B31, 10 ng; Lane 7—plasmid 2H1, 100 ng; Lane 8—*B. hermsii*, 100 ng. The sizes and mobilities of pBR322 standards (Lane 1) are indicated to the left of each figure. Curvature of the bands mimics the dye front and thus represents a gel distortion rather than variation in size of amplified fragments.
Figure 3B:
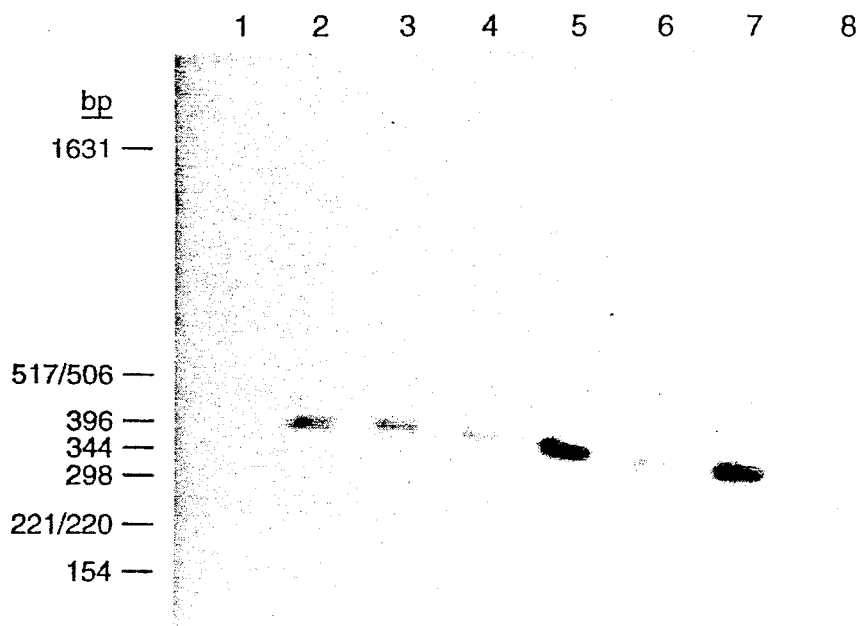

The hybridization analyses indicated that any of the B. burgdorferi sequences present in the clones could be potential targets in a PCR assay specific for Lyme disease spirochetes. However, the insert in clone 2H1 (Table 1) was selected as the sequence from which to develop a PCR assay. The nucleotide sequence of this insert and the positions of the oligo primers used in the PCR assay are shown in FIG. 2. Assay conditions were optimized using the cloned 2H1 sequence as template. FIG. 3A represents an ethidium-bromide stained agarose gel on which were run the PCR products from genomic DNA of four different B. burgdorferi strains and B. hermsii. A single fragment which co-migrates with the product of the plasmid 2H1 is present with amplified B. burgdorferi DNA after 15 cycles of amplification (FIG. 3A, lanes 2–7). No amplified products are present even after 30 cycles with B. hermsii DNA (FIG. 3A, lane 8). To confirm that the amplified DNA fragments are legitimate products, a Southern blot prepared from this gel was hybridized to a probe from the middle of the target sequence (FIG. 2, oligo B). An autoradiograph of this blot is shown in FIG. 3B. The PCR amplified fragment from B. burgdorferi DNA hybridizes to this probe. Hence, the PCR assay developed from cloned 2H1 sequences efficiently amplifies a specific target segment of B. burgdorferi genomic DNA.

Specificity of PCR Assay

Figure 4B:
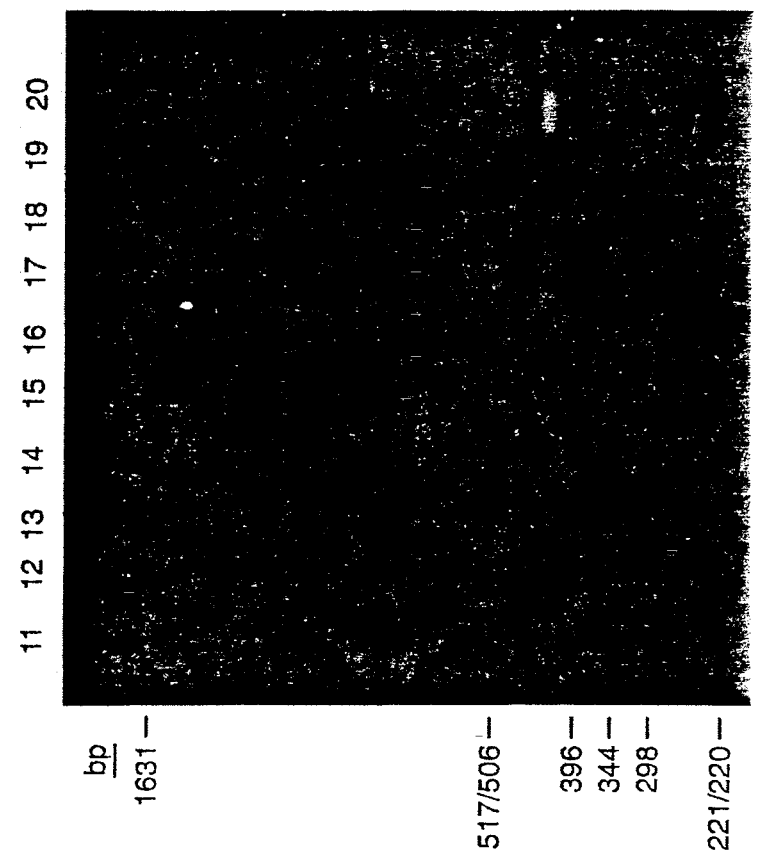
FIGS. 4(A-B) demonstrate the specificity of *B. burgdorferi* PCR assay. 100 ng of genomic DNA from eight different strains of *Borrelia burgdorferi* (A) as well as from other members of the genus Borrelia (B) was amplified for 20 cycles and 1/10 of the reaction analyzed on a gel. The source of template DNA in each reaction was as follows: Lane 2—*B. burgdorferi* SH.2.82 (tick isolate); Lane 3—*B. burgdorferi* JD.1 (tick isolate); Lane 4—*B. burgdorferi* ECM.NY.86 (human skin isolate); Lane 5—*B. burgdorferi* CA.2.87 (tick isolate); Lane 6—*B. burgdorferi* B31 (tick isolate; Lane 7—*B. burgdorferi* HB19 (human blood isolate); Lane 8—*B. burgdorferi* G1 (human cerebral spinal fluid isolate); Lane 9—*B. burgdorferi* G2 (human cerebral spinal fluid isolate); Lane 10—O DNA control; Lane 12—*B. hermsii* HS1 (relapsing fever); Lane 13—*B. hermsii* FG (relapsing fever); Lane 14—*B. parkeri* (relapsing fever); Lane 15—*B. turicatae* (relapsing fever); Lane 16—*B. coriaceae* (epidemic bovine abortion); Lane 17—*B. crocidurae* (relapsing fever); Lane 18—*B. anserina* (bird spirochete); Lane 19—0 DNA control; Lane 20—*B. burgdor-* feri B31. Hin F pBR322 standards were run in lanes 1 and 11; sizes and mobilities of fragments are indicated to the left of each figure.
Figure 4A:
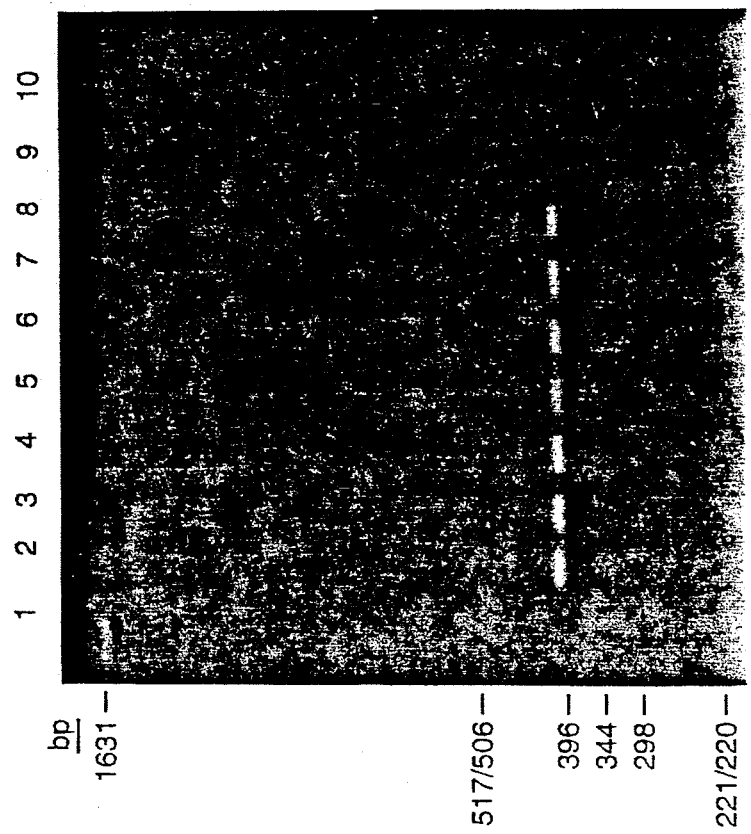

Purified DNA from eight different B. burgdorferi strains was amplified by PCR and the products visualized with ethidium bromide on an agarose gel (FIG. 4A). These include four North American tick isolates (lanes 2, 3, 5 and 6), a North American human skin isolate (lane 4), a North American human blood isolate (lane 7, and two European human cerebral spinal fluid isolates (lanes 8 and 9). An amplified product of approximately 370 bp is present with seven of eight strains. Hence, B. burgdorferi isolates from a broad geographic area and of both tick and human origin are detected with this assay.

Purified DNA from other members of the genus Borrelia was amplified by PCR and products visualized with ethidium bromide on an agarose gel (FIG. 4B). These include four species which cause relapsing fever in humans, a bird spirochete and a spirochete responsible for bovine epidemic abortion. No amplified fragments are present after 20 cycles for any of these spirochetes (FIG. 4B, lanes 12–19) in contrast to the B. burgdorferi positive control (lane 20). Similar results are obtained even after 40 cycles of amplification (data not shown). These results clearly demonstrate the specificity of this assay for the Lyme disease spirochete.

Sensitivity of Assay

Figure 5A:
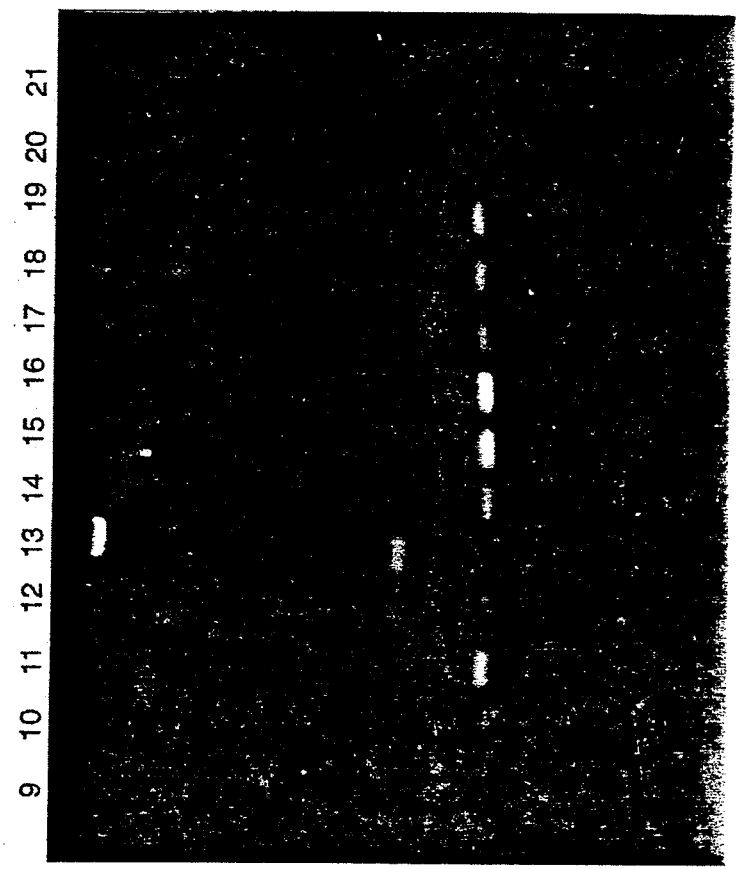

In order to determine the sensitivity of the assay, PCR amplification was performed on serially diluted B. burgdorferi DNA ranging from 100 ng to 1 pg. Amplifications were repeated for 15 to 30 cycles, depending upon the dilution. Products were visualized with ethidium bromide on an agarose gel (FIG. 5A). As little as 1 pg of target DNA is amplified to visually detectable levels after 30 cycles. Since 1/20 of the PCR reaction was analyzed on the gel, this actually represents the product from 0.05 pg DNA. It is estimated that this corresponds to about 25 organisms by considering the yield of total DNA from a stationary phase culture with $10^9$ organisms per ml. Continued cycles of amplification should, therefore, allow the detection of a single organism. A zero DNA negative control reaction does not have an amplified fragment (FIG. 5A, lane 8).

Figure 5B:
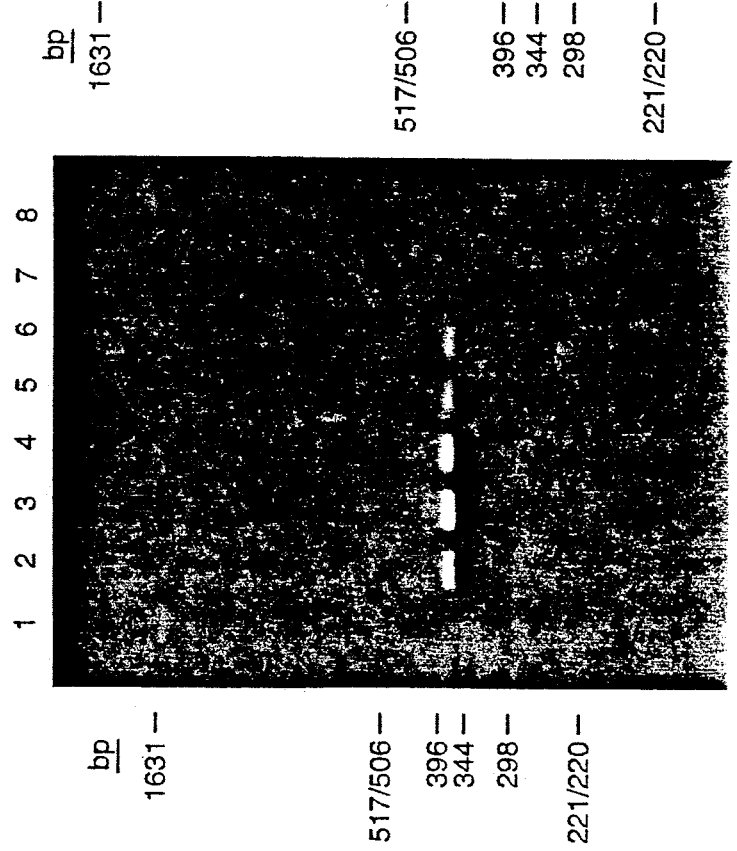

It was also determined if the target sequence could be amplified directly from lysed spirochetes without any purification of the DNA and what the sensitivity of such a procedure would be. To test this, approximately $10^8$ bacteria were lysed by heating, serially diluted and PCR amplified for 15 to 45 cycles, depending upon the dilution. Reaction products were visualized with ethidium bromide on an agarose gel (FIG. 5B, lanes 14–21). An amplified fragment was seen with as little as $10^{-3}$ microliter of crude lysate by 35 cycles (lane 19). The amount run on the gel corresponds to the amplified product from approximately 50 bacteria. Hence, this assay is capable of amplifying directly from limited numbers of lysed B. burgdorferi without purifying the DNA.

PCR Assay in the Presence of Eukaryotic DNA

A highly specific and sensitive PCR assay for B. burgdorferi will be useful only if it retains these features in the presence of DNA from host tissues. To assess this, the amplification of target sequences from 100 ng B. burgdorferi DNA was compared in the presence of 0, 100 and 1000 ng of eukaryotic DNA (FIG. 6A, lanes 4, 3 and 1). A single fragment is amplified equally well in all three cases. Dilutions of B. burgdorferi DNA ranging from 10 ng to 0.1 pg were amplified for 20–40 cycles in the presence of 100 ng eukaryotic DNA (FIG. 6A, lanes 5–14). An amplified fragment of appropriate mobility is present in all cases. However, by 40 cycles of amplification, some additional products are present (lane 14). These are present in the negative control sample as well, which contains 100 ng of eukaryotic DNA and no B. burgdorferi DNA (lane 15). This negative control sample also contains a fragment the same size as the anticipated B. burgdorferi PCR product. However, unlike the legitimate product, this fragment is not cleaved by the restriction enzyme HindIII (data not shown).

Figure 6B:
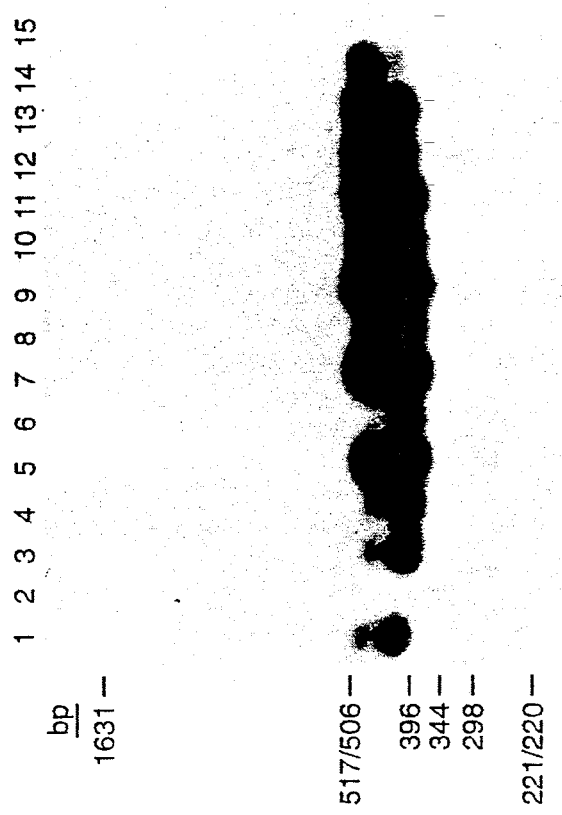
Figure 6A:
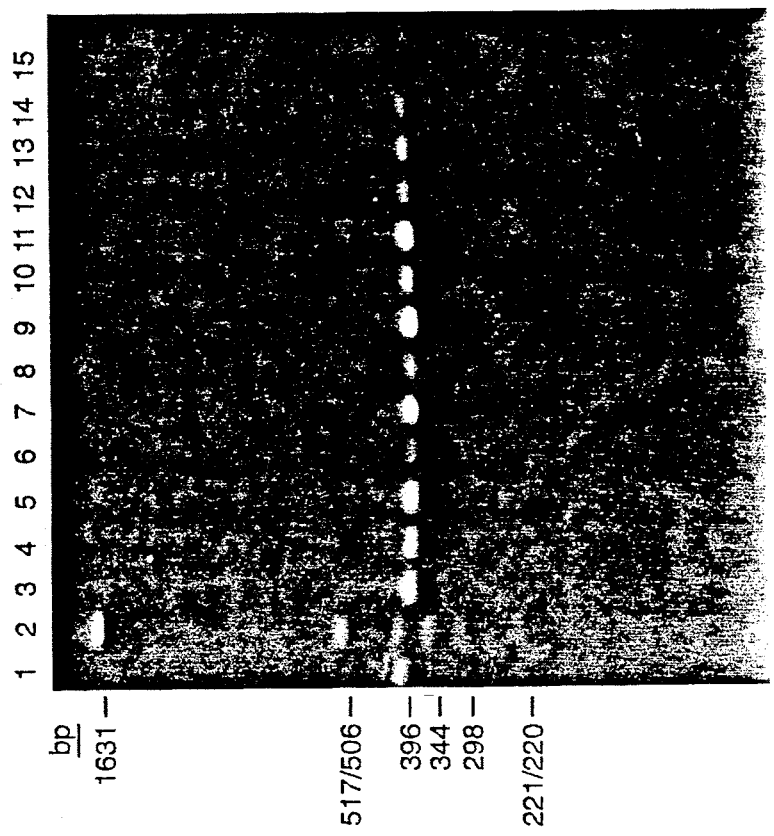

In order to establish the identity of the amplified products, a blot prepared from this gel was hybridized to a probe from the middle of the target sequence (FIG. 6B). This probe hybridizes to only the anticipated fragment from samples containing B. burgdorferi DNA (FIG. 6B, lanes 5–14). There are no hybridizing sequences present in the negative control sample, eliminating the possibility of contaminating DNA (FIG. 6B, lane 15). Hence, when in doubt, confirmation of the validity of the amplified products by hybridization may be advisable when exogenous DNA is present. The hybridization data indicate, however, that 0.1 pg of B. burgdorferi DNA (approximately four organisms) can be detected in the presence of a 10⁶-fold excess of eukaryotic DNA.

In summary, the results presented herein clearly demonstrate the efficacy of a sensitive and specific PCR assay for identifying Lyme disease spirochete from randomly cloned *B. burgdorferi* DNA sequences. The assay provides a rapid means of determining whether spirochetes present in ticks, rodents, birds, etc. are actually *B. burgdorferi*. Of course, a similar approach could be taken to develop PCR assays specific for other species of Borrelia.

It is quite remarkable that the sensitivity of the PCR assay described herein extends down to a few copies of *B. burgdorferi* DNA, even in the presence of a vast excess of eukaryotic DNA. Surprisingly, the crude lysates of *B. burgdorferi* are equally efficiently amplified; hence, extensive sample preparation is not necessary. However, it is desirable that a proper negative control be included in an assay which is sensitive to a few molecules. Since 1 ng of a cloned sequence represents approximately $10^8$ copies, care must be taken to avoid introducing artefactual positives with contaminating DNA, and their absence must always be demonstrated by including proper controls in the assay.

A diagnostic kit for Lyme disease, in accordance with the present invention, comprises the following components:

1. Unique components in accordance with the present invention:
   a. Oligonucleotide primers designated A and C in FIG. 2, or any other set of primers derived from the sequence of 2H1.
   b. Internal oligonucleotide to confirm the identify of a PCR amplified fragment, designated B in FIG. 2, or any other probe derived from the sequence of 2H1.
   c. Positive control template DNA, which comprises plasmid DNA from the clone 2H1. This DNA could also be used as a probe for the detection or to confirm the identity of *B burgdorferi* DNA.
2. Necessary commercially available reagents.
   a. Components of the PCR reaction buffer (cocktail) as described in the manufacturer's instruction manual or other workable cocktail.
   b. DNA polymerase-TAQ, Klenow or the like.
   c. Reverse transcriptase, if RNA is to be detected.

It is noted that the PCR per se is a well known technique and this technique as such is not a subject of the present invention.

A method of detecting the presence of *B. burgdorferi* spirochete in a specimen comprises the following steps.
A. Purify DNA or RNA from the sample to be tested, and assay less than 10 micrograms per 100 microliter of PCR reaction mix. If RNA is to be tested, a cDNA copy must first be made with reverse transcriptase. or
B. Directly boil a de-paraffinated, formalin-fixed sample in TE buffer (10 mM Tris, 1 mM EDTA, pH8) for 10 minutes, centrifuge to remove particulate matter, and assay an aliquot of the supernatant in the PCR reaction. or
C. Liberate DNA directly from unfixed samples by cell lysis with heat or other suitable means. Test directly in the PCR assay without further purification.

It should be noted that the above-mentioned steps are not exclusive of other means of sample preparation which are compatible with the PCR assay. The appropriate protocol will vary with different sample sources.

The PCR reaction comprises repeated cycles of thermal denaturation, primer annealing, and polymerase extension (TAQ), as described by the manufacturer (Cetus) and the accompanying instructions. Nested sets of oligo primers can be substituted sequentially to give greater specificity when necessary. Aliquots of the PCR reaction mix can be removed after various cycles and checked for the presence of an amplified, *B. burgdorferi*-specific fragment. The PCR conditions described herein are not exclusive and others which will work well will be known to the artisan.

It is noted that a deposit of the clone 2H1 has been made at the ATCC, Rockville, Md., on May 16, 1989, under accession number ATCC 67984. The deposit shall be viably maintained, replacing if it becomes nonviable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

TABLE I

Hybridization of clones to *B. burgdorferi* and *B. hermsii* DNA[1]

| | | | *B. burgdorferi* strains | | | | | |
|---|---|---|---|---|---|---|---|---|
| Clone | Insert-bp | Genomic origin[2] | B31 | SH.2.82 | HB19 | G1 | G2 | *B. hermsii* |
| 2H11 | 127 | chromosome | + | + | + | + | + | − |
| 2H4 | 150 | chromosome | + | + | + | + | + | − |
| 2H1 | 379 | chromosome | + | + | + | + | + | − |
| 2H20 | 2400 | chromosome | + | + | + | + | + | +/− |
| 2H7 | 7400 | chromosome | + | + | + | + | + | +/− |
| 2H6 | 1000 | 19 kb plasmid | + | + | + | + | + | − |
| 2H14 | 1000 | 49 kb plasmid | + | + | + | + | + | − |
| 3A18 | 1300 | 19 kb plasmid | + | + | +˙ | + | + | − |

[1]Hybridization data were obtained by genomic Southern and dot blot analyses.
[2]Plasmid designation refers to *B. burgdorferi* strain B31 from which these clones were derived. The hybridizing species of plasmids in other strains varied somewhat in size.

What is claimed is:

1. An isolated DNA segment consisting of the DNA sequence

⟶
              A
5' GATCAAAA|CG AAGATACTAA ATCTGT|AATT
3' CTAGTTTTGC TTCTATGATT TAGACATTAA

```
                GCAGAAACAC CTTTTGAATT
                CGTCTTTGTG GAAAACTTAA

51  AAATTTTGGC TTGTCAGGAG CCTATGGAAA
     TTTAAAACCG AACAGTCCTC GGATACCTTT

CGAGACATTC AATAATTCAT
                GCTCTGTAAG TTATTAAGTA

101  CAATAACATA CTCTTTAAAA GATAAATCCG
     GTTATTGTAT GAGAAATTTT CTATTTAGGC

TAGTTGGCAA CGATTTATTG
                ATCAACCGTT GCTAAATAAC

151  AGCCCAACTT TATCAAATTC TGCAATTTTA
     TCGGGTTGAA ATAGTTTAAG ACGTTAAAAT

GCATCTTTTG GAGCTAAATA
                CGTAGAAAAC CTCGATTTAT

201  TAAGCTTGGA TTAACAAAAA TAAACGATAA
     ATTCGAACCT AATTGTTTTT ATTTGCTATT

AAATACCTAT CTTATTTTGC
                TTTATGGATA GAATAAAACG

251  AAATGGGAAC TGATTTTGGA ATAGATCCTT
     TTTACCCTTG ACTAAAACCT TATCTAGGAA
     ←B

TTGCAAGGGA TTTTTCTATA
                AACGTTCCCT AAAAAGATAT

301  TTTGGACACA TCTCAAAAGC AGCGAATTTC
     AAACCTGTGT AGAGTTTTCG TCGCTTAAAG

AAAAAAGAAA CACCCTCAGA
                TTTTTTCTTT GTGGGAGTCT

351  TCCTAACAAA AAAGCTGAAA TATTTGATC 3'
     AGGATTGTTT TTTCGACTTT ATAAACTAG 5'
     ←C
``` which hybridizes with DNA of *Borrelia burgdorferi* origin, and which does not cross hybridize with other Borrelia species.

2. A cloned DNA segment of the sequence of claim 1 and fragments derived from said sequence and specifically hybridizable therewith.

3. The fragments of claim 2 consisting of the sequences

```
5' CGAAGATACTAAATCTGT 3'
5' AATCAGTTCCCATTTGCA 3'
5' GATCAAATATTTCAGCTT 3'
```

4. The cloned DNA of claim 2 having ATCC deposit no. 67984.

5. A diagnostic kit for the detection of *Borrelia burgdorferi* DNA, comprising a first container containing the nucleotide sequence, having the sequence of claim 1, and a second container containing oligonucleotide primers derived from said sequence for employing in the polymerase chain reaction assay.

6. A method for detecting presence or absence of *Borrelia burgdorferi* in a specimen comprising:
   a) purifying the DNA from the specimen suspected of *Borrelia burgdorferi* infection;
   b) adding the DNA obtained from step (a) to a polymerase chain reaction reaction mixture containing primers for amplifying *Borrelia burgdorferi*-specific DNA of the sequence of claim 1;
   c) amplifying by polymerase chain reaction;
   d) testing aliquots of the polymerase chain reaction reaction product from step (c) for the presence or absence of *Borrelia burgdorferi*-specific amplified DNA by conventional means including gel electrophoresis and hybridization with a labeled probe internal to the amplified fragment, wherein a positive detection of said *Borrelia burgdorferi*-specific DNA being indicative of the presence of *Borrelia burgdorferi* in said specimen.

* * * * *

UNITED STATES PATENT AND TRADEMARK OFFICE
CERTIFICATE OF CORRECTION

PATENT NO.   :   5,279,938
DATED        :   January 18, 1994
INVENTOR(S)  :   Patricia A. Rosa It is certified that error appears in the above-identified patent and that said Letters Patent is hereby corrected as shown below:

On the title page: Item [75]

Change inventors to

-- Patricia A. Rosa, Hamilton, Montana, and
   Tom G. Schwan, Hamilton, Montana --

Signed and Sealed this

Fourteenth Day of June, 1994

Attest:

BRUCE LEHMAN

*Attesting Officer*          Commissioner of Patents and Trademarks